United States Patent [19]

Drope et al.

[11] 4,384,283
[45] May 17, 1983

[54] METHOD AND AN APPARATUS FOR MONITORING THE SUBJECTION OF INDIVIDUAL PEOPLE TO HARMFUL GASES

[75] Inventors: Eckard Drope, Cologne; Karl P. Jansky, Muensing; Wilhelm Pross, Munich, all of Fed. Rep. of Germany; Wolfram Breuer, deceased, late of Leverkusen, Fed. Rep. of Germany, by Gisela Breuer, Axel W. Breuer, Ingo R. Breuer, executors

[73] Assignees: Bayer Aktiengesellschaft, Leverkusen; Compur-Electronic GmbH, Munich, both of Fed. Rep. of Germany

[21] Appl. No.: 154,344

[22] Filed: May 29, 1980

[30] Foreign Application Priority Data

Jun. 12, 1979 [DE] Fed. Rep. of Germany ....... 2924367

[51] Int. Cl.³ ............................................. G08B 17/10
[52] U.S. Cl. ........................................ 340/632; 73/23; 204/1 T; 204/406; 340/573
[58] Field of Search ............... 340/632, 633, 634, 518, 340/573; 364/497, 498; 250/337, 396, 388, 392; 73/23; 204/1 T, 195 R

[56] References Cited

U.S. PATENT DOCUMENTS 3,068,450 12/1962 Fletcher et al. ................ 340/518 X
3,878,496 4/1975 Erickson ........................ 250/388 X
4,231,249 11/1980 Zuckerman ..................... 340/632 X Primary Examiner—John W. Caldwell, Sr.
Assistant Examiner—Daniel Myer
Attorney, Agent, or Firm—Sprung, Horn, Kramer & Woods

[57] ABSTRACT

A method for monitoring the exposure of an individual person to toxic gases is carried out such that the gas concentration is continuously measured with a sensor for the specific gas, recorded and the measured values then read and evaluated. Instantaneous values of the concentration are periodically scanned, temporal mean values of the instantaneous values are formed over a predetermined time interval, these mean values are stored and an alarm triggered if the instantaneous value and/or the mean value exceeds a predetermined critical value over the time interval or an integral multiple thereof.

10 Claims, 1 Drawing Figure

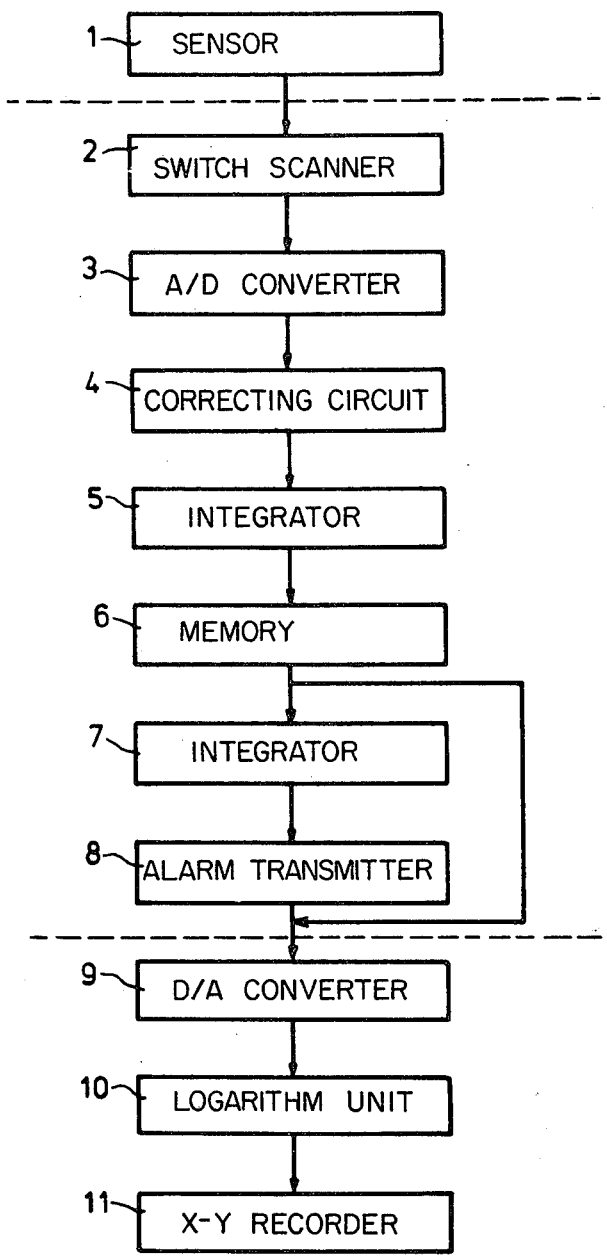

METHOD AND AN APPARATUS FOR MONITORING THE SUBJECTION OF INDIVIDUAL PEOPLE TO HARMFUL GASES

BACKGROUND OF THE INVENTION

The invention relates to a method for monitoring the exposure of an individual person to toxic gases. The invention also relates to an apparatus for carrying out the monitoring operation.

In many industrial plants, the employees are exposed to most various loadings with toxic gases. The exposure of a person to a toxic gas is physically defined as the time integral of the respective gas concentration measured in the vicinity of the person. The total exposure accumulated during the respective person's working or shift period or a temporal mean value derived from it is of particular interest. Gas detectors for protecting workers, which are worn on the employee's body, differ greatly in design and in performance, the measuring principle being the most decisive factor for the desired information. There are some detectors which trigger an alarm when the maximum allowable concentration of a toxic gas is exceeded in the work place. These detectors usually employ electrochemical sensors which are distinguished by short response times (U.S. Pat. No. 4,141,800). Integrating devices which determine the layer mean value are also known. These devices are based on an air sample collector with which the air prevailing in the work place is drawn continuously through an absorber by means of a small pump. The poisonous substance to be recorded is fixed in the absorber (Offenlegungsschrift No. 26 58 739.3).

Moreover, there is a commercial device which records on a strip of indicator paper the concentration gradient in the form of discoloration of the paper strip. The concentration gradient can then be read by a photometer and recorded. The temporal resolution is determined by the speed of travel of the paper. In a more recent version of this device, the photometer is combined with the detector and triggers an alarm when the mean value exceeds a critical value during the averaging time determined by the speed of travel. An alarm is thus emitted if a specific gas dosage (the product of gas concentration and duration of action) is exceeded during the averaging time predetermined by the device. This alarm function is hereinafter called dosage warning for the sake of simplicity.

According to the prior art, therefore, the various measuring problems, i.e. the detection of the instantaneous value concentration with the emission of an alarm when the critical value is exceeded, the dosage warning, and the detection of the concentration gradient and the layer average value, are solved using various devices. However, it is important to combine all these measures when monitoring a person with respect to exposure to toxic gas, the weighing and the averaging periods having to be determined specifically for each gas. Although with acutely toxic substances there lies the serious consideration of instantaneous warning, an important factor for cumulatively acting substances with an average half-life value, is the adjustment of the correct warning dosage. On the other hand, the warning function is less important in the case of the markedly cumulatively acting substances. In the final analysis, the concentration gradient is detected for a quite different purpose, namely to discover operations which are associated with particularly strong gas subjection. Only a short temporal resolution (a few minutes) is needed for this purpose as, otherwise, the unsystematic short variations would produce a false picture. In the final analysis, the shift mean value (8 hour mean value) can be compared in terms of definition with the MAK (also known as the Threshold Limit Value (TLV) value.

Another complication arises from the fact that quite different measuring methods often have to be adopted for different working substances (gases). A complete program of devices for the protection of workers therefore consists of the most varied components.

SUMMARY OF THE INVENTION

Accordingly, an object of the invention is to develop a method and a device based thereon which finds a solution to the three part problem, i.e. instantaneous value alarm, dosage warning and establishment of the concentration profile for any sensors based on a device of uniform design.

This object is achieved according to the invention by the combination of the following measures:
 (a) The instantaneous values of the gas concentration detected by the sensor are scanned discontinuously but periodically.
 (b) The scanned instantaneous values are averaged over a predetermined time interval $\tau$.
 (c) The mean value thus formed is stored.
 (d) If the instantaneous value of the gas concentration and/or the mean value over $\tau$ or $n\tau$ exceeds a predetermined critical value, an alarm is triggered. In this case, n represents an integral multiple ($n = 2, 3, 4 \ldots$).

Further developments of the invention as well as a device which is suitable for carrying out the method according to the invention are described hereinafter in more detail.

The technical progress of the invention lies in the form of the solution to the problem of protecting individual workers. Based on this solution, a toxic gas dosage warning device which can be worn on the body and which has alarm functions (instantaneous value alarm and mean value alarm) on the one hand and allows subsequent recording of the exposure gradient (gas concentration as a function of time) on the other hand, has been proposed for the first time. The recorded data can then be processed by an external computer, for example, to determine long term mean values. The method according to the invention fulfills the conditions for carrying out the above-mentioned functions electronically in a single device. When transferring to another gas component, it is necessary merely to exchange the sensor.

The device affords the further advantage that it can easily be modified depending on the requirements of the specific gas. Thus, for example, in the case of acutely toxic gases, an alarm is triggered whenever the instantaneous value exceeds the critical value, while in the case of cumulatively acting gases the alarm is triggered whenever the mean value is exceeded. Finally, the possibility of miniaturization is of great practical importance. The fundamental design can be produced in a relatively small housing using modern electronic means. In this case, two viewpoints are decisive:
 1. Only mean values and not instantaneous values are stored. A relatively small memory capacity is thus sufficient.

2. The memory is scanned by an external evaluating center to which the device can be connected.

Thus, only the operations of scanning the measured value, forming the mean value, storage and the alarm functions are integrated in the device. This separation is an important condition for minimizing the overall volume.

BRIEF DESCRIPTION OF THE DRAWINGS

An embodiment of the invention is described below with reference to the attached block diagram.

A sensor 1 producing an electric signal which increases with the concentration, serves to detect the gas concentration. Electro-chemical sensors of the type described, for example, in U.S. Pat. No. 4,141,800 are preferably used for this purpose. The measured value is periodically scanned by a switch 2. The switching cycle preferably amounts to 1 to 2 seconds. Lower switching frequencies, i.e. longer cycle times (up to 10 seconds) can be adopted only in the case of very slow changes of concentration. The scanned measured values are then digitalized in an analogue-digital converter 3 and linearization is carried out by means of a correcting circuit 4 if the sensor 1 has a non-linear characteristic. The correcting circuit 4 thus linearize the characteristic curve. The measured values which have been modified and digitalized in this way are fed to an integrator 5 which integrates the measured values over a predetermined time interval $\tau$ to form a mean value. The time interval $\tau$ is selected in such a way that the systematic concentration gradient is visible whereas the instantaneous value variations are suppressed. The time constant of the sensor must also be taken into consideration when selecting $\tau$. It is preferable for $\tau$ not to lie below the order of magnitude of the sensor time constant. In practice, time intervals $\tau$ of one and a half to two minutes are selected for foming the mean value. The mean values formed are transferred into a memory 6. The stored measured values are then averaged again in a second integrator 7, averaging taking place over a substantially longer time interval $n\tau$ (with $2 \leq n \leq 40$). n is determined in accordance with the toxicity of the gas to be measured. In the event of doubt, relatively small n-values have to form the basis for critical gases. The step completed in the integrator 7 should be designated as fluid mean value formation over the time interval $n\tau$. A comparator which compares the fluid mean value with a predetermine critical value and triggers an alarm signal (alarm transmitter 8) when the critical value is exceeded is connected to the integrator 7.

The components 2 to 8 are combined in a structural unit which is supplied as an extra device for the gas detector 1. This extra device is a dosimeter having an alarm function (8) and a fitted memory (6), depending on its function. A second alarm transmitter (not shown) can be connected directly to the sensor and gives a warning if the instantaneous value of the gas concentration exceeds the critical value.

The mean values stored in 6 can also be read with the aid of an external evaluating center and recorded. The evaluating center consists of a D/A-converter 9, a logarithm unit 10 and a X-Y-recorder 11. The measured values scanned by the memory 6 are firstly converted into analog values (9), then converted into logarithms (10) and finally recorded by the X-Y recorder 11. The conversion into logarithms allows the concentration gradient to be plotted clearly over several decades. Additional complementary processing of the measure value, for example, the formation of an 8-hour mean value, can be performed in the evaluating center. Alternatively, the 8-hour mean value can also be formed in the dosage warning device (2–8).

The practical manipulation of the system proceeds in the following manner. At the beginning of the working day, the functioning of the sensor 1 is firstly checked using a test gas generator. The sensor is then combined with the dosage warning device (components 2 to 8) and worn on the respective person's body for the entire working period. Alarm signals are triggered if predetermined critical values are exceeded in the instantaneous value concentration and in the mean value concentration. At the end of the working day, the dosage warning device (2 to 8) is disconnected from the gas detector 1 and inserted into the evaluating center 9, 10, 11. The stored measured values are then read therein, in the manner described, and an individual print out is then produced about the gas burden on the respective person during a working day. It can be seen that this system is easy to manage, offers considerable protection from manipulation and supplies a clear print out due to the reduction in data brought about by the compaction of the measured value. Thus, external means of adjustment are not provided in practice in the dosage warning device. The device parameters $\tau$ and $n.\tau$ as well as the critical values for triggering the alarm are firmly adjusted at the factory and cannot be manipulated by the wearer of the device. The device combining the gas detector, dosage warning device and evaluating center is used, for example, in the chemical industry, for monitoring people whe are exposed during their working period to unexpected charges of toxic gases at low concentrations.

We claim:

1. In a method for monitoring the exposure of an individual person to toxic gases, wherein the gas concentration is continuously measured using a sensor for the specific gas, recorded, and the measured values are then read and evaluated, the improvement comprising the steps of:
   (a) periodically scanning instantaneous values of the concentration;
   (b) forming temporal mean values of the instantaneous values over a predetermined time interval $\tau$, wherein 50 sec. $\leq \tau \leq$ 150 sec. and $\tau$ is greater than the time for each scan;
   (c) storing the mean values;
   (d) averaging the mean values taken over an interval which is an integral multiple n of $\tau$ wherein $2 \leq n \leq 40$; and
   (d) triggering an alarm when a value formed in step (a) exceeds a first predetermined critical value and triggering an alarm when a result of step (d) exceeds a second predetermined critical value.

2. A method according to claim 1, comprising periodically scanning every 1 to 10 seconds.

3. A method according to claim 1, further comprising the step of linearizing the instantaneous values before forming the temporal mean values.

4. A method according to claim 1, wherein the step of periodically scanning comprises scanning every 1 to 2 seconds and the step of forming the mean value comprises using an interval $\tau$ in the range of from 80 to 100 seconds.

5. An apparatus for monitoring the exposure of an individual person to toxic gases, comprising:

(a) a sensor for converting gas concentration into a continuous analog electrical signal;
(b) switching means for periodically scanning the electric signal coming from the sensor;
(c) an A/D-converter for digitalizing each scanning signal value;
(d) a first integrator for integrating the digitalized measured values for forming a mean value over a predetermined time interval $\tau$ wherein 50 sec. $\leq \tau \leq$ 150 sec. and $\tau$ is greater than the time for each scan;
(e) memory means for storing the mean values from the first integrator;
(f) a second integrator for forming the average mean value over a time interval which is an integral multiple n of $\tau$ wherein $2 \leq n \leq 40$; and
(g) means for comparing the scanned values with a first predetermined critical value and for producing an alarm signal when the first critical value is exceeded and for comparing the average means value formed by the second integrator with a second predetermined critical value and for producing an alarm signal when the second critical value is exceeded.

6. An apparatus according to claim 5, further comprising means for linearizing the digitalized values prior to applying same to the first integrator.

7. An apparatus according to claim 5, wherein the switching means, A/D-converter, the integrators, memory means and comparator are combined in one housing.

8. An apparatus according according to claim 5, further comprising a device for effecting visual evaluation of the apparatus measurements including a D/A-converter connected to the output of the memory means, a logarithm circuit and a measured value visual indicator.

9. An apparatus according to claim 5, wherein the scanning means scans the electrical signal every 1 to 10 seconds.

10. An apparatus according to claim 5, wherein the scanning means scans the electrical signal every 1 to 2 seconds and wherein $80 \leq \tau \leq 100$.

* * * * *